United States Patent [19]

Frangatos

[11] 4,098,707

[45] Jul. 4, 1978

[54] LUBRICANT COMPOSITION

[75] Inventor: Gerassimos Frangatos, Cherry Hill, N.J.

[73] Assignee: Mobil Oil Corporation, New York, N.Y.

[21] Appl. No.: 789,172

[22] Filed: Apr. 20, 1977

[51] Int. Cl.$^2$ .................. C10M 1/10; C10M 3/02; C10M 5/02; C10M 7/02
[52] U.S. Cl. ............................................. 252/49.9
[58] Field of Search ......................................... 252/49.9

[56] References Cited

U.S. PATENT DOCUMENTS 3,663,439 5/1972 Frangatos .................. 252/49.9

FOREIGN PATENT DOCUMENTS 1,052,751 12/1966 United Kingdom ............... 252/49.9

*Primary Examiner*—Delbert E. Gantz
*Assistant Examiner*—Irving Vaughn
*Attorney, Agent, or Firm*—Charles A. Huggett; Raymond W. Barclay; Claude E. Setliff

[57] ABSTRACT

The antiwear and load carrying properties of lubricants are improved by incorporating therein a product prepared by reacting a chlorinated wax with a trihydrocarbyl phosphite.

8 Claims, No Drawings

LUBRICANT COMPOSITION

BACKGROUND OF THE INVENTION

1. Field of the Invention

The invention relates to lubricants having desirable antiwear and load carrying properties. It more particularly relates to improving such properties by adding a small amount of chlorinated wax-phosphite reaction product.

2. Description of the Prior Art

Lubricants are subject to heavy stresses that can affect their antiwear and load carrying ability. Thus, there has been considerable effort to discover classes of compounds that will aid in retaining or, preferably, in improving these important properties.

For example, sulfur compounds have been used for the purpose, as is taught in U.S. Pat. No. 3,697,499. Unfortunately, the presence of sulfur in lubricants may cause severe metal corrosion, especially copper. To overcome this, special processes have been used to moderate the effect of sulfur, as in U.S. Pat. No. 3,697,499, or other materials have been used, among them certain phosphorus compounds, as lubricant additives. U.S. Pat. No. 3,663,439, for instance, discloses lubricating oils whose extreme pressure properties have been improved by adding thereto a reaction product involving a trihydrocarbyl phosphite.

SUMMARY OF THE INVENTION

The invention provides a lubricant composition comprising lubricant and an antiwear amount of a product prepared by reacting a chlorinated wax with a trihydrocarbyl phosphite.

DESCRIPTION OF SPECIFIC EMBODIMENTS

The waxes useful in preparing the agent of this invention will generally have an average molecular weight within the range of from about 400 to about 3000 and will mostly comprise hydrocarbons having from 20 to 150 carbon atoms. These will have a chlorine content ranging between about 28% and 70% by weight. Depending on the chlorine content, the chlorinated waxes will vary in consistency from viscous oils to low melting solids, and their density and viscosity will also vary accordingly. In general, waxes containing a substantial amount of chain branching will not be completely acceptable for this invention because the chlorinated product therefrom tends to be unstable.

The trihydrocarbyl phosphite useful in this invention will have the formula:

$(RO)_3P$ where R is a hydrocarbyl group containing from 1 to about 20 carbon atoms. Preferred are the lower alkyl groups, i.e., those having 1 to 6 carbon atoms. Also included are those containing aryl groups, e.g., phenyl, naphthyl and anthryl and the alkyl-substituted members, the alkyl containing 1 to 6 carbon atoms. Specifically, the useful reactants include the trimethyl, triethyl, tributyl, trihexyl, trioctyl, tridecyl, trianthryl, tritolyl and tri(alkylphenyl) phosphites.

The reaction used to produce the product useful in this invention is the Michaelis-Arbusov reaction or rearrangement. It may be generalized by the following:

where R has the above meaning and R′ is the wax molecule. It will be understood that the presentation of the phosphonate structure here is not a disclosure that the product made from chlorinated wax has a definite structure. While it is believed that the product formed is a phosphonate, its structure is much more complex than is indicated by the above equation, especially in view of the fact chlorine remains in the final product.

Useful products can be made by reacting from about 0.25 moles to about 2 moles of chlorinated wax, preferably 0.50 moles, with one mole of trihydrocarbyl phosphite. The temperature of reaction will range from about 150° C to about 220° C, preferably about 170° C to about 185° C, depending upon the reactants used. Also, the reaction times will vary between about 1 hour to about 6 hours, preferably between about 1 to about 2 hours, again depending upon the particular reactants chosen. The refluxing temperature of the trihydrocarbyl phosphite is in most cases the preferable reaction temperature. The final reaction product will contain from about 10% to about 60% chlorine and from 1% to about 10% phosphorus. While no extraordinary purification steps are required, removal of the hydrocarbyl halide formed is desirable because it can interfere with the primary Arbusov reaction.

The lubricants which are improved by the reaction products of this invention are mineral and synthetic lubricating oils and greases therefrom. The mineral oils will be understood to include not only the paraffinic members, but also the naphthenic members. By synthetic oils are meant synthetic hydrocarbons, polyalkylene oxide oils, polyacetals, polysilicones and the like, as well as synthetic ester oils. Included among the latter type are those esters made from monohydric alcohols and polycarboxylic acids, such as 2-ethylhexylazelate and the like. Also included are those esters made from polyhydric alcohols and aliphatic monocarboxylic acids. Those of this group are especially important and in this group are found esters prepared from (1) the trimethylols, such as the ethane, propane and butane derivatives thereof and 2,2-disubstituted propane diols and (2) the pentaerythritols reacted with aliphatic monocarboxylic acids containing from about 4 to 9 carbon atoms. Mixtures of these acids may be used to prepare the esters. Preferred among the esters are those made from pentaerythritol and a mixture of $C_5$–$C_9$ acids.

As has been indicated, the reaction products disclosed herein are useful as antiwear and load carrying agents. When so used, they may be added in amounts sufficient to impart such properties to the lubricant. Generally, the useful amount will range from about 0.25% to about 10% by weight, preferably from about 0.5% to about 2%, of the product.

Having discussed the invention in broad and general terms, the following are offered to illustrate it. It is to be understood that the Examples are merely illustrative and are not intended to limit the scope of the invention.

EXAMPLE 1

One hundred and fifty grams of a cracked wax containing 40.6% by weight of chlorine, a molecular weight of 610 and a viscosity at 210° F of 150–160 seconds and 50 g (0.2 mole) of tributyl phosphite were heated under nitrogen with stirring at 185°–190° C for two hours. The clear, yellowish solution was cooled and kept at room temperature, under nitrogen, overnight. The following day stirring under nitrogen at 185° C was resumed and continued for four hours. 18 g of phosphite was recovered when the contents were placed under house vacuum. 173 g of a clear, yellowish fluid was obtained. It should be noted that throughout the heating cycle, butyl chloride was distilling off.

The product had a chlorine content of 31.1% and a phosphorus content of 4.35%.

EXAMPLE 2

One hundred and eighty grams (0.34 mole) of the cracked wax of Example 1 and 50 g of triethyl phosphite (0.3 mole) were placed in a flask and heated at 170°–175°C under nitrogen with continuous stirring for four hours. House vacuum was applied and 26 g of the phosphite was collected. This was returned to the reaction flask, the contents of which were then cooled to room temperature and kept under nitrogen overnight. Stirring at 170–175 under nitrogen was begun and maintained for an additional three hours. Distillation gave 22.0 g of the phosphite and 193 g of a viscous, dark brown residue. The residue had a chlorine content of 37.8% by weight and a phosphorus content of 1.82% by weight.

EVALUATION OF THE PRODUCTS

The product of Example 1 was tested in the 4-Ball Test using a modified 4-Ball machine. In this test, three stationary balls are placed in a lubricant cup and a lubricant containing the additive to be tested is added thereto. A fourth ball is placed on a chuck mounted on a device which can be used to spin the ball at known speeds and loads.

To a 100 cc sample of a lubricating oil comprising an 80–20 mixture, respectively, a 150″ solvent paraffinic bright mineral oil (at 210° F) and 200″ solvent paraffinic neutral mineral oil (at 100° F) was added sufficient of the product of Example 1 (containing 4.35% by weight of P). Table I summarizes the results.

The product of Example 2 was tested under the same conditions and in the same oil. Results are summarized in Table II.

TABLE I

| Temperature | Room Temperature | | | | 200° F | | | |
|---|---|---|---|---|---|---|---|---|
| RPM | 500 | 1000 | 1500 | 2000 | 500 | 1000 | 1500 | 2000 |
| Load, Kg | 60 | 60 | 60 | 60 | 60 | 60 | 60 | 60 |
| Time, min. | 30 | 30 | 30 | 30 | 30 | 30 | 30 | 30 |

TABLE I-continued

| Temperature | Room Temperature | | | | 200° F | | | |
|---|---|---|---|---|---|---|---|---|
| RPM | 500 | 1000 | 1500 | 2000 | 500 | 1000 | 1500 | 2000 |
| Average Scar Diameter, mm | | | | | | | | |
| Horizontal 1 | 0.40 | 0.50 | 0.60 | 0.60 | 0.40 | 0.50 | 0.60 | 0.60 |
| 2 | 0.40 | 0.50 | 0.60 | 0.60 | 0.40 | 0.50 | 0.60 | 0.60 |
| 3 | 0.40 | 0.50 | 0.60 | 0.60 | 0.40 | 0.50 | 0.60 | 0.60 |
| Vertical 1 | 0.40 | 0.50 | 0.60 | 0.60 | 0.40 | 0.50 | 0.60 | 0.60 |
| 2 | 0.40 | 0.50 | 0.60 | 0.60 | 0.40 | 0.50 | 0.60 | 0.60 |
| 3 | 0.40 | 0.50 | 0.60 | 0.60 | 0.40 | 0.50 | 0.60 | 0.60 |
| Final Average | 0.40 | 0.50 | 0.60 | 0.60 | 0.40 | 0.50 | 0.60 | 0.60 |

TABLE II

| | Room Temperature | | | | 200° F | | | |
|---|---|---|---|---|---|---|---|---|
| RPM | 500 | 1000 | 1500 | 2000 | 500 | 1000 | 1500 | 2000 |
| Average Scar Diameter, mm | | | | | | | | |
| Horizontal 1 | 0.40 | 0.50 | 0.50 | 0.60 | 0.50 | 0.60 | 0.60 | 0.60 |
| 2 | 0.40 | 0.50 | 0.50 | 0.60 | 0.50 | 0.60 | 0.60 | 0.60 |
| 3 | 0.40 | 0.50 | 0.50 | 0.60 | 0.50 | 0.60 | 0.60 | 0.60 |
| Vertical 1 | 0.40 | 0.50 | 0.50 | 0.60 | 0.50 | 0.60 | 0.60 | 0.60 |
| 2 | 0.40 | 0.50 | 0.50 | 0.60 | 0.50 | 0.60 | 0.60 | 0.60 |
| 3 | 0.40 | 0.50 | 0.50 | 0.60 | 0.50 | 0.60 | 0.60 | 0.60 |
| Final Average | 0.40 | 0.50 | 0.50 | 0.60 | 0.50 | 0.60 | 0.60 | 0.60 |
| Average Scar Diameter, mm | | | | | | | | |
| Untreated Oil | | | | | | | | |
| Final Average | 0.50 | 0.60 | 0.88 | 2.34 | 0.60 | 1.06 | 1.86 | 2.23 |

I claim:

1. A lubricant composition comprising a lubricant and an antiwear amount of a product prepared by reacting a chlorinated wax and a trihydrocarbyl phosphite.

2. The composition of claim 1 in which the wax has a molecular weight of from about 400 to about 3000.

3. The composition of claim 2 in which the chlorine content of the chlorinated wax is from about 28% to about 70% by weight.

4. The composition of claim 1 wherein said product contains from about 10% to about 60% chlorine by weight.

5. The composition of claim 1 wherein said product contains from about 1 to about 10% phosphorus by weight.

6. The composition of claim 1 in which the trihydrocarbyl phosphite is a trialkyl phosphite, the alkyl group containing from 1 to 6 carbon atoms.

7. The composition of claim 6 in which the trialkyl phosphite is triethyl phosphite.

8. The composition of claim 6 in which the trialkyl phosphite is tributyl phosphite.

* * * * *

UNITED STATES PATENT AND TRADEMARK OFFICE
CERTIFICATE OF CORRECTION

PATENT NO. : 4,098,707
DATED : July 4, 1978
INVENTOR(S) : GERASSIMOS FRANGATOS

It is certified that error appears in the above-identified patent and that said Letters Patent are hereby corrected as shown below:

Column 4, line 20      "Horizontal" should read
(Table II)      --Horizontal 1 --.

Signed and Sealed this

Sixteenth Day of January 1979

[SEAL]

Attest:

RUTH C. MASON
Attesting Officer

DONALD W. BANNER
Commissioner of Patents and Trademarks